United States Patent [19]

Ganglbauer et al.

[11] 4,295,375
[45] Oct. 20, 1981

[54] ULTRASONIC METHOD OF TESTING WELDED JOINTS

[75] Inventors: Otto Ganglbauer; Felix Wallner, both of Linz; Helmut Scheidl, Ried; Hermann Reindl, Linz, all of Austria; Rainer Frielinghaus, Bornheim-Merten, Fed. Rep. of Germany

[73] Assignees: Voest-Alpine Aktiengesellschaft, Linz, Austria; Krautkraemer GmbH, Cologne, Fed. Rep. of Germany

[21] Appl. No.: 106,865

[22] Filed: Dec. 26, 1979

[30] Foreign Application Priority Data

Jan. 8, 1979 [AT] Austria ................................ 115/79

[51] Int. Cl.³ ............................................. G01N 29/04
[52] U.S. Cl. ....................................... 73/582; 73/627
[58] Field of Search ................. 73/582, 588, 596, 597, 73/598, 599, 600, 618, 620, 624, 625, 627, 628, 629, 632

[56] References Cited

U.S. PATENT DOCUMENTS

| 2,545,309 | 3/1951 | Roberts | 73/600 |
| 3,895,685 | 7/1975 | Gillette et al. | 73/627 |
| 4,170,143 | 10/1979 | Ries et al. | 73/629 |

*Primary Examiner*—Stephen A. Kreitman
*Attorney, Agent, or Firm*—Kurt Kelman

[57] ABSTRACT

Welded joints of austenitic steels are tested by ultrasonic sound caused to be incident on the joint at an oblique angle thereto. Information regarding the size and nature of reflectors in the joint can be derived from the amplitude of the echoes generated at the reflectors in response to the sound beam. To ensure a definite relationship between the amplitude of the echoes and the nature and size of the reflector, the frequency of the sound use for testing is below and upper frequency limit at which the wavelength of sound in the base material equals the largest peak-to-valley distance of the base metal weld interface in any of the consecutive areas of the interface on which the sound beam is incident at any time.

6 Claims, 3 Drawing Figures

ULTRASONIC METHOD OF TESTING WELDED JOINTS

This invention relates to an ultrasonic method of testing welded joints, particularly joints of austenitic steel, wherein the sound waves consisting preferably of longitudinal waves are directed onto the joint at an oblique angle thereto and the amplitudes of the resulting echo pulses are measured as indications of the approximate size and nature of the reflector. The invention relates also to a seam weld which is adapted to be tested by the method.

The testing of seam welds by transverse waves which are directed onto the joint at an oblique angle thereto permits a highly selective detection of faults in seam welds consisting of ferritic steels but does not permit such selective detection of faults in seam welds of austenitic steel because the coarser structure of the seam weld of austenitic steel gives rise to interference so that even large faults generally cannot be detected. The ultrasonic testing of austenitic welded joints has been greatly improved by the use of longitudinal waves which are directed onto the joint at an oblique angle thereto. In that case, the signal-to-noise ratio of the echo amplitudes has been further improved by the use of special sound transducer heads comprising suitable electroacoustic transducers. The selectivity with which faults in austenitic seam welds can be detected has been greatly improved by the use of such special sound transducer heads. On the other hand, it has not been possible to analyze the echo amplitudes for the size and nature of the fault because the amplitudes of the echoes which are received are highly independent from the size and nature of the reflector.

It is an object of the invention to avoid these disadvantages and so to improve an ultrasonic method of testing welded joints, which is of the kind described first hereinbefore, that a proper dependence of the echo amplitudes on the nature and size of the reflector is ensured.

This object is accomplished according to the invention in that the frequency of the sound used for testing is below an upper frequency limit, at which the wavelength of sound in the base material equals the largest peak-to-valley distance of the base metal-weld interface in any of the consecutive areas of said interface on which said sound beam is incident at a time.

The invention is based on the recognition that owing to the known differences between the velocities of sound in the base material and in the weld the sound waves are refracted at the base metal-weld interface so that owing to the inevitable waviness of said interface the sound rays are deflected in different directions, depending on their angles of incidence. This phenomenon gives rise to interference and to partly considerable changes of the amplitudes from those which would be obtained in case of an undisturbed propagation of sound. Surprisingly it has been found that the interference which changes the amplitudes can be decreased to a nondisturbing value if the wavelength of the sound is not in excess of the largest peak-to-valley distance of the base material-weld interface in the area on which the sound beam is incident at a time. If the frequency of the sound used for testing is below the frequency limit that is determined by said peak-to-valley distance, the echo amplitudes will depend as desired on the size and nature of the reflector. As the sound transducer heads are operated at a frequency which is selected in consideration of the velocity of sound in the base material, the upper frequency limit which must not be exceeded if the object of the invention is to be accomplished is related to the wavelength of sound in the base material. Whereas strictly speaking the upper frequency limit depends on the wavelength of sound at the interface or in the weld, the velocity of sound at that interface and in the weld are not known in general. The selection of the upper frequency limit in dependence on the velocity of sound in the base material introduces an error but this is so small that it can be neglected in practice.

It is believed that the fact that disturbing interferences which appreciably change the echo amplitudes do not arise unless the wavelength of sound exceeds the peak-to-valley distance of the base metal-weld interface in the area on which the sound is incident at a time is due to the presence of sound beams rather than discrete sound rays so that only the sum effect of the interferences rather than the individual interferences can be detected. Nevertheless, an increase of the wavelength of sound corresponding to a decrease of its frequency sound waves will further decrease the influence of the interference. For this reason, particularly favorable conditions will be obtained if the frequency of the sound used for testing is less than one-half of the frequency limit. The decrease of the frequency of the sound used for testing is limited by the desired resolution, which depends on the wavelength of the sound beam.

To permit the use of sound at the desired high frequencies for testing, an excessive waviness of the base metal-weld interface in the area on which the sound beam is incident at a time must be avoided. To permit the use of sound at the conventional frequency for testing, the seam welds to be tested by the method should be so designed that the base metal-weld interface is substantially planar and its largest peak-to-valley distance in any area on which the sound beam is incident at a time does not exceed the wavelength of sound in the base material at conventional testing frequencies. As has been stated above, only the peak-to-valley distance of the interface in any area on which the sound beam is incident at a time is significant. For this reason the base metal-weld interface need not be exactly planar but may have a curvature if such curvature is so gentle that the peak-to-valley distance consisting of the difference in height between the lower portion defined by the sound beam and the apex does not exceed the wavelength of the sound beam.

The invention is illustrated by way of example on the drawing, in which

Figure 1:
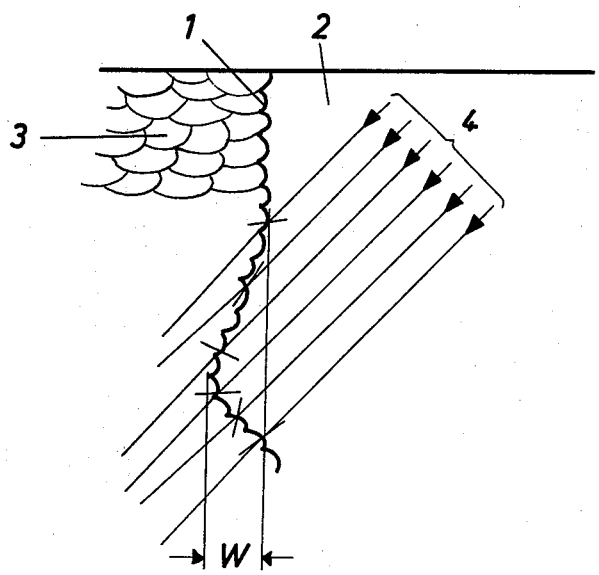
FIG. 1 is a diagrammatic sectional view showing basically the refraction of sound rays at an interface between a base material and a weld.

It is apparent from FIG. 1 that in a welded joint the interface 1 between the base material 2 and the weld 3 does not exactly conform to the theoretical configuration of the seam but has a waviness which is due to the penetration of the several weld beads. As a result, a sound beam 4 which is directed onto the joint at an oblique angle thereto is refracted at the interface 1 because the sound travels at different velocities in the base material 2 and the weld 3. This refraction of several sound rays is diagrammatically indicated in FIG. 1, which shows that owing to the waviness and the non-planarity of the interface the several sound rays are deflected in different directions, depending on the angle of incidence of each sound ray on the interface. This phenomenon results in an interference of the sound rays so that the amplitudes of the sound rays are changed. As a result, the amplitude of an echo which has been generated in response to the sound and is subsequently received depends not only on the size and nature of the reflector but also on that of the interference. Because the influence of these interferences during the test cannot be estimated, the echo amplitudes will not permit any conclusion to be drawn concerning the nature and size of the reflector if relatively strong interferences occur.

The occurrence of disturbingly large interferences can be avoided if the wavelength of the sound beam 4 is selected in consideration of the waviness of the interface 1. The largest peak-to-valley distance W of the interface 1 in any area on which the sound beam 4 is incident at a time defines an upper frequency limit for the sound used for testing. If the depth-to-valley distance W of the interface 1 in any such area is less than the wavelength of sound and preferably less than one-half of the wavelength of sound, the disturbing influence of the interference will be negligible so that the echo amplitudes will be an indication of the nature and size of the reflector. Because the velocity of sound depends on the material and establishes a direct relationship between the frequency and wavelength of sound, the largest peak-to-valley distance W determines an upper frequency limit for the sound used for testing. The wavelength is related to the base material 2 as the velocity of sound in the base material is generally known whereas the actually significant velocity of sound at the base metal-weld interface or in the weld is not known. Whereas this gives rise to an error, the latter is not significant particularly at frequencies below the upper frequency limit.

Figure 2:
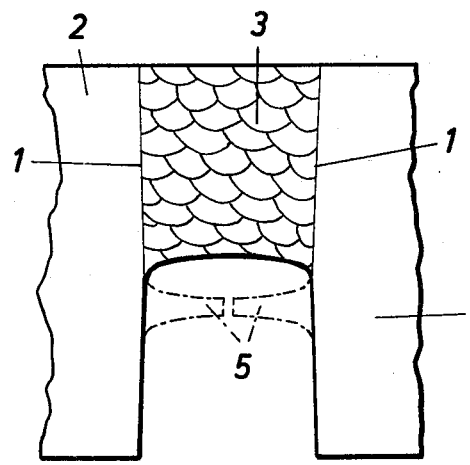
FIG. 2 shows a bell seam weld in accordance with the invention.

When it is desired to use sound at the usual frequencies for testing, the peak-to-valley distance of the interface 1 in any area on which the sound beam is incident at a time must be sufficiently small. This can be accomplished by the provision of base metal-weld interfaces which are as planar as possible and by the selection of suitable welding conditions. FIG. 2 shows a bell seam, which is particularly suitable for an ultrasonic test because the interfaces 1 are planar except for a waviness which in any area on which the sound beam is incident at a time has a largest peak-to-valley distance not in excess of the wavelength of sound at the frequencies which are usual for testing. In order to form such interface 1, the root zone is removed, in accordance with FIG. 2, so that the original lands 5 are entirely eliminated and the constrictions otherwise formed in the base metal-weld interfaces are avoided.

Figure 3:
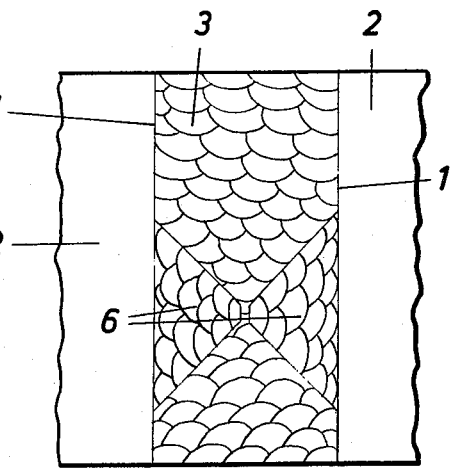
FIG. 3 shows a double-V butt joint according to the invention.

When it is desired to form a double-V seam, as shown in FIG. 3, weld ribs 6 are deposited on the flat end faces of the base material 2. These weld ribs 6 constitute the lands required to form the seam weld. The weld ribs 6 have no influence on the interference if the weld ribs 6 exhibit the same acoustic behavior as the remaining weld. It will be understood that such weld deposits can be used also for other types of seams.

Because only the largest peak-to-valley distance W within any area of the base metal-weld interface on which the sound beam 4 is incident at any given time is significant, the base metal-weld interfaces need not be planar but may have any curvature within the largest peak-to-valley distance which is determined by the upper frequency limit. The teaching of the invention to select the frequency of the sound used for testing in consideration of the waviness of the base metal-weld interface may be used to advantage where different velocities of sound give rise to a refraction of the sound beam at the base metal-weld interface and this refraction would result in interferences which change the sound amplitudes and the amplitude of the resulting echoes so that the latter may not properly indicate the size and nature of the reflector.

What is claimed is:

1. A method of testing a welded joint comprising base metal and a weld bonded to said base metal at an interface, said method comprising the steps of causing an ultrasonic sound beam to be incident on said interface at an oblique angle to said joint, receiving echoes generated by reflectors in said joint in response to said beam, and deriving information regarding the size and nature of such reflectors from the amplitude of said echoes, the improvement residing in that the frequency of said sound beam is below an upper frequency limit at which sound has in said base material a wavelength which equals the largest peak-to-valley distance of said interface in any area thereof on which said sound beam is incident at a time.

2. The improvement set forth in claim 1 when applied to a welded joint which said joint comprises austenitic steel.

3. The improvement set forth in claim 1 in a method in which said ultrasonic sound beam is constituted by longitudinal sound waves.

4. The improvement set forth in claim 1, in which the frequency of said sound is lower than one-half of said upper frequency limit.

5. In a seam weld comprising base metal and a weld bonded to said base metal at an interface, said seam weld being adapted to be tested by a method comprising the steps of causing an ultrasonic sound beam at a conventional frequency below a predetermined upper frequency limit, to be incident on said interface at an oblique angle to said joint in response to said beam, and deriving information regarding the size and nature of such reflectors from the amplitude of said echoes, the improvement residing in that the largest peak-to-valley distance of said interface in any area thereof on which said sound beam is incident at a time is not in excess of the wavelength of sound in said base material at said predetermined upper frequency limit.

6. In a method of making and testing a welded joint comprising base metal and a weld bonded to said base metal at an interface, wherein an ultrasonic sound beam is caused to be incident on said interface at an oblique angle to said joint, echoes generated by reflectors in said joint in response to said beam are received, and information regarding the size and nature of such reflectors is derived from the amplitude of said echoes, the improvement residing in that said interface is formed to have in any area thereof on which said sound beam is incident at a time a peak-to-valley distance which is not in excess of a predetermined maximum and the frequency of said sound beam is below an upper frequency limit at which sound has in said base material a wavelength which is not in excess of said predetermined maximum peak-to-valley distance.

* * * * *